United States Patent [19]

Levy

[11] Patent Number: 5,176,257

[45] Date of Patent: * Jan. 5, 1993

[54] SPECIMEN SLIDE PACKAGE

[76] Inventor: Abner Levy, 325 N. Oakhurst Dr., P4, Beverly Hills, Calif. 90210

[ * ] Notice: The portion of the term of this patent subsequent to Dec. 11, 2007 has been disclaimed.

[21] Appl. No.: 706,890

[22] Filed: May 29, 1991

Related U.S. Application Data

[63] Continuation-in-part of Ser. No. 552,332, Jul. 13, 1990, Pat. No. 5,050,735.

[51] Int. Cl.$^5$ .............................................. B65D 85/48
[52] U.S. Cl. .................................. 206/456; 206/478; 206/482
[58] Field of Search .............................. 206/449–456, 206/472, 477, 478, 482; 229/92.1, 92.3, 92.7, 92.8

[56] References Cited

U.S. PATENT DOCUMENTS

| | | | |
|---|---|---|---|
| 1,141,172 | 6/1915 | Clark | 229/92.8 |
| 2,198,138 | 4/1940 | Sutton | 206/482 |
| 2,298,601 | 10/1942 | Tremblett | 229/92.8 |
| 2,559,776 | 7/1951 | Larzelere | 229/92.1 |
| 2,985,288 | 5/1961 | Reich | 206/363 |
| 3,913,732 | 10/1975 | Peterson | 206/0.83 |
| 4,078,656 | 3/1978 | Crane et al. | 206/456 X |
| 4,429,787 | 2/1984 | Morse | 206/0.83 |
| 4,976,354 | 12/1990 | Levy | 206/456 |
| 5,050,735 | 9/1991 | Levy | 206/456 |

Primary Examiner—Bryon P. Gehman
Attorney, Agent, or Firm—Beehler & Pavitt

[57] ABSTRACT

A package for a medical specimen slide is constructed of a sheet including side panels and end panels joined to a central base portion, with latching portions for holding all the panels in a packaged condition, and a specimen slide is inserted through two rectangular openings and under a retaining band for holding the slide against the base portion. The openings are dimensioned for easy insertion and secure holding of the slide and the package is sized so that the slide holds the end and side panels spaced away from the specimen on the slide.

11 Claims, 5 Drawing Sheets

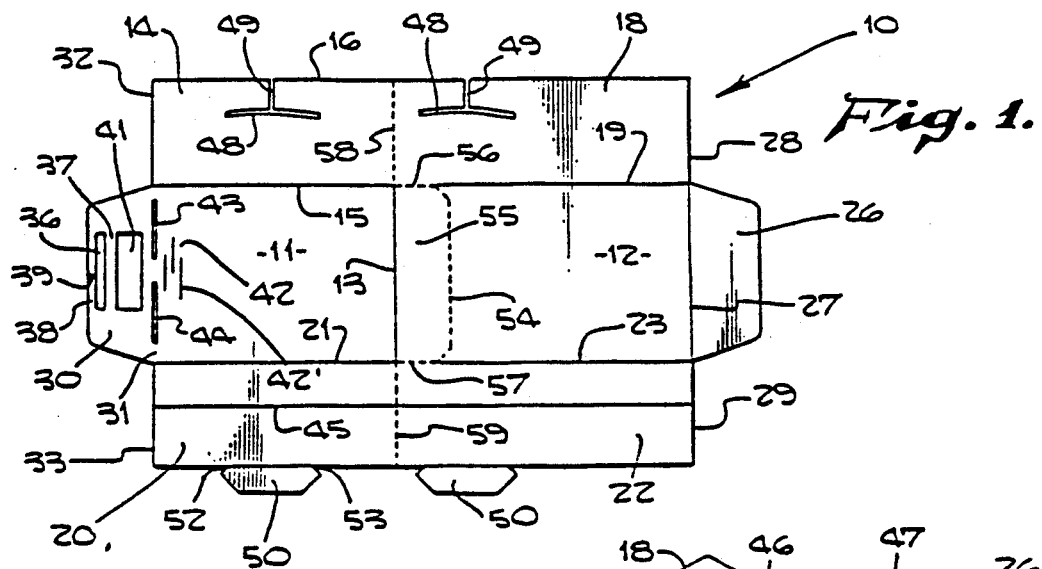
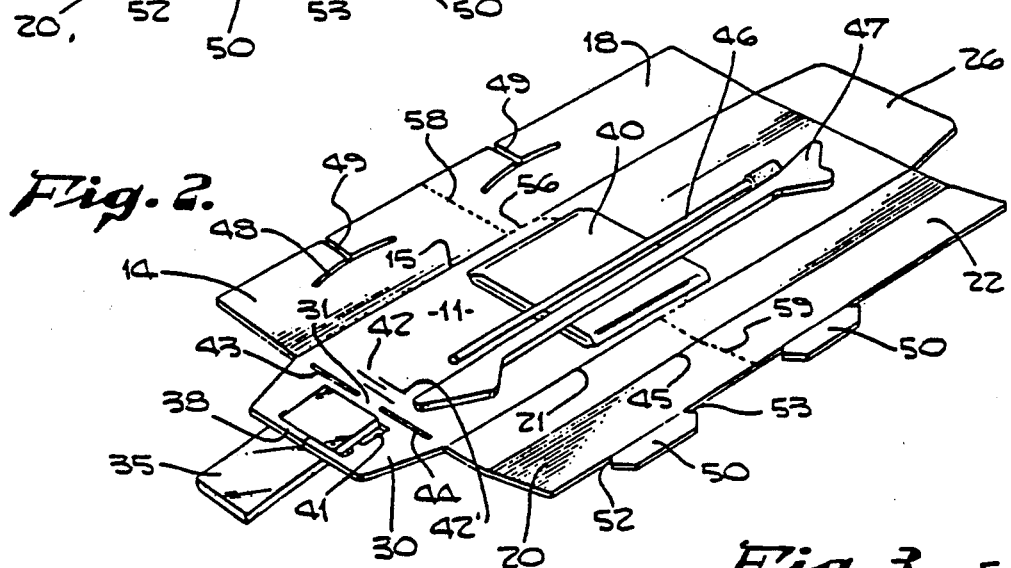
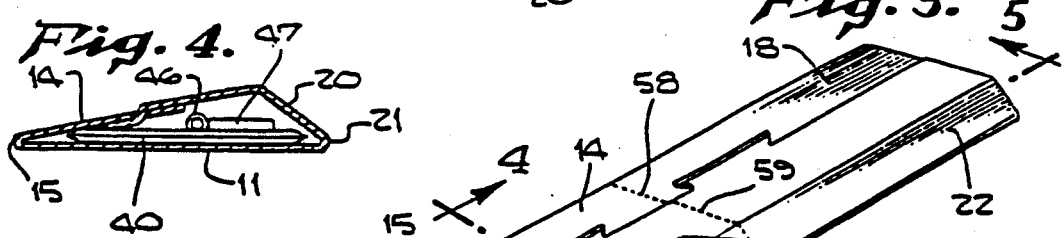
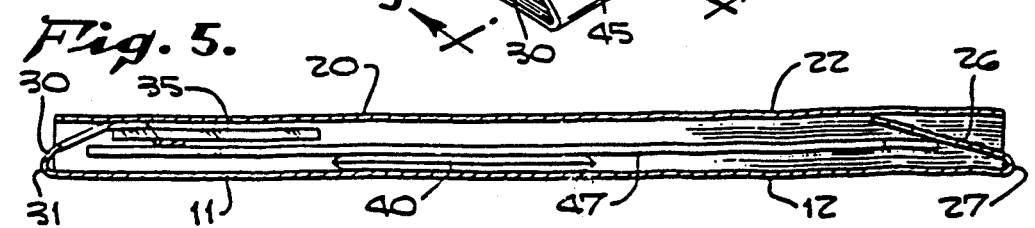

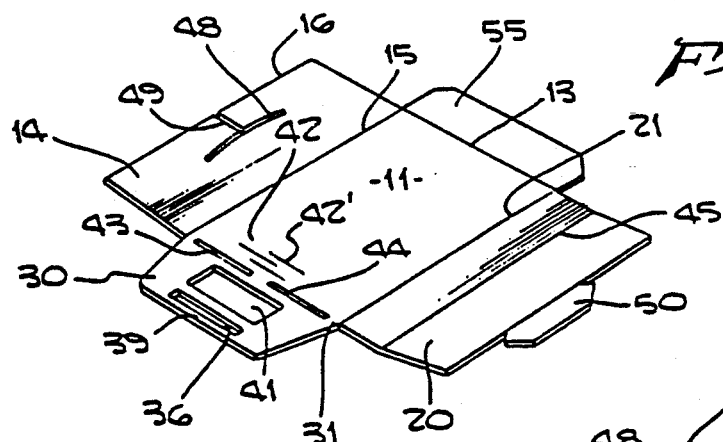
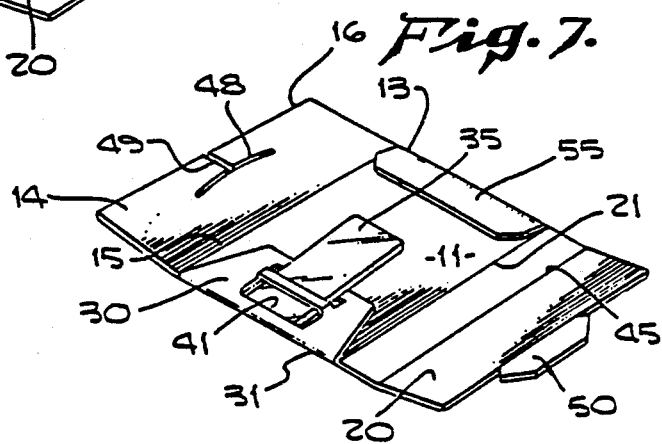
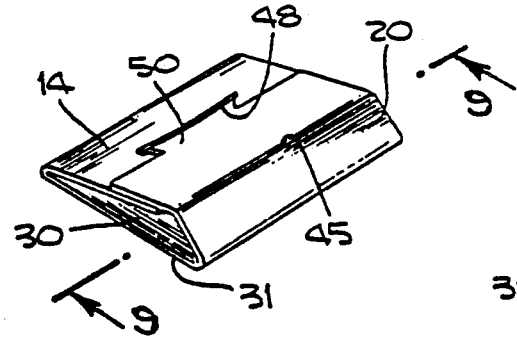
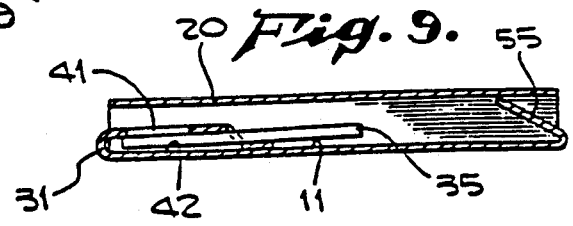
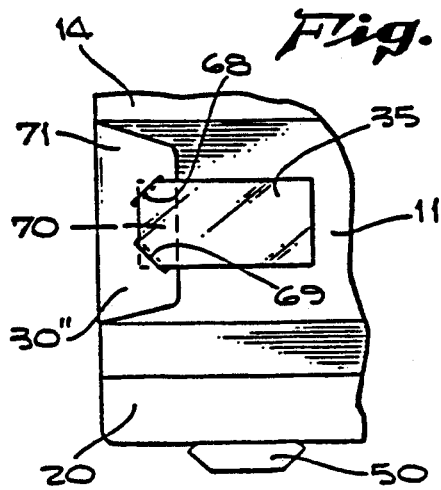
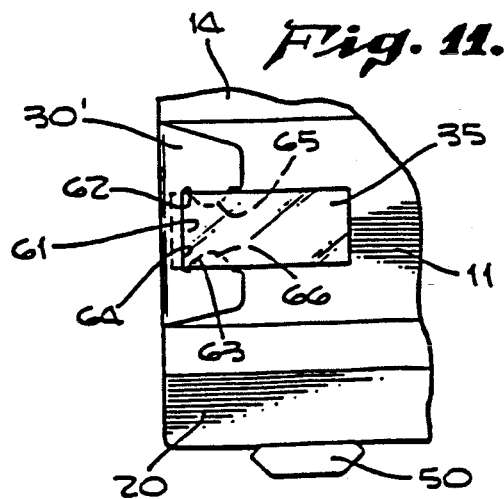

SPECIMEN SLIDE PACKAGE

This is a continuation-in-part of application Ser. No. 552,332, filed Jul. 13, 1990, now U.S. Pat. No. 5050735.

For the handling of specimens for laboratory analysis in the medical and related fields, current practice is to have as much of the necessary paraphernalia as possible of a disposable character. Although biological and medical specimens in the final stage ready for microscopic or other examination may be compact and require little space for preservation and handling, that circumstance may not prevail during preparation for and collection of the specimen. This is to say that for the collection of a specimen, the technician frequently has need for instruments, swabs, disinfectants, patches and the like, necessary for requiring the needed scraping, tissue or fluid accumulation which, once having been used, is no longer needed and can be disposed of.

Conversely, the specimen itself whether one for microscopic examination or chemical analysis, need only be very small, needs only modest means for preservation and requires a correspondingly small package in which to preserve it and deliver it for analysis.

It is therefore among the objects of the invention to provide a new and improved reusable-type package for acquisition and retention of a specimen, parts of which are readily disposable when no longer needed.

Another object of the invention is to provide a new and improved reusable package for the acquisition and retention of a specimen, which features a relatively larger package in which all necessary paraphernalia needed for acquisition of the specimen can be carried, but which is separable so as to leave only a relatively smaller package for the finally acquired specimen, by means of which it can be delivered to a laboratory for analysis.

Another object of the invention is to provide a new and improved reusable-type specimen package wherein an effective mounting for a specimen slide is provided in such manner that it is handily located and well protected during both the collecting stage as well as the final use stage and which is accompanied by adequate and readily available means for identification.

Still another object of the invention is to provide a new and improved reusable-type specimen package which is compact when filled with the necessary paraphernalia, and further which is of such character that it can be divided into a smaller compact package for containing only the specimen, permitting the surplus packaging to be disposed of.

Still further among the objects of the invention is to provide a new and improved reusable-type specimen package of adequate proportions to contain collection of paraphernalia and the final specimen, which is easily and readily manipulatable during collection and final disposition, relatively inexpensive and readily disposable as to those portions which may no longer be needed once the specimen has been collected and ready for delivery to the laboratory.

With these and other objects in view, the invention consists of the construction, arrangement and combination of the various parts of the device serving as examples only of one or more embodiments of the invention, whereby the objects contemplated are attained, as hereinafter disclosed in the specification and drawings, and pointed out in the appended claims.

In the Drawings:

FIG. 1 is a plan view of the sheet of material cut to shape and size for the package.

FIG. 2 is a perspective view of the sheet of material equipped for initial packaging.

FIG. 3 is a perspective view of the initially formed package.

FIG. 4 is a cross-sectional view on the line 4—4 of FIG. 3.

FIG. 5 is a longitudinal sectional view on the line 5—5 of FIG. 3.

FIG. 6 is a perspective view of that portion of the sheet of material used for the final package.

FIG. 7 is a view similar to FIG. 6, but partly folded over for packaging.

FIG. 8 is a perspective view of a completed final package.

FIG. 9 is a longitudinal sectional view on the line 9—9 of FIG. 8.

FIG. 10 is a fragmentary plan view of a second form of the sheet of material as equipped for packaging.

FIG. 11 is a fragmentary plan view of a third form of the sheet of material as equipped for packaging.

Figure 12:
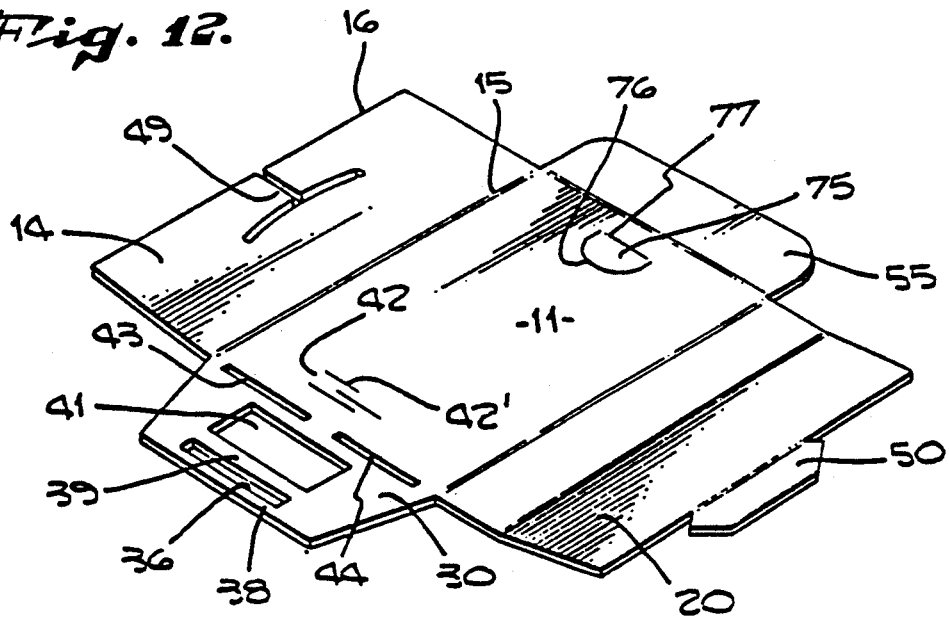
FIG. 12 is a perspective view of that portion of the sheet of material used for the final package of a modified form of the device.

In an embodiment of the invention chosen for the purpose of illustration there is shown a sheet of packaging material for assembly into a specimen package indicated generally by the reference character 10, which consists essentially of a single sheet of package material specially cut for folding in a distinctive fashion. The package is made up of two central base portions 11 and 12 separated by a transverse fold line 13. The two base portions together form, in effect, a long rectangular bottom for the package in its initial form. On one side of the base portion 11 is a side panel 14 with a captive side edge joined by a fold line 15 to a corresponding side edge of the base panel 11, leaving a free edge 16.

Similarly, for the base portion 12 there is a side panel 18 with a captive side edge joined by a fold line 19 to a corresponding side edge of the base portion 12. The fold lines 15 and 19 are continuous with respect to each other forming one fold line for the combined side panels 14 and 18 permitting them to be folded over the initially joined base portions 11 and 12.

On the opposite side of the base portion 11 is a side panel 20 having a captive edge joined to a corresponding edge of the base portion 11 along a fold line 21. Again, for the base portion 12 there is a side panel 22 joined along a fold line 23 to a corresponding edge of the base portion 12. It is of consequence to note in this connection that the combined width of the side panels 14 and 20 is materially greater than the width of the corresponding base portion 11. Similarly, the combined width of the side panels 18 and 22 is materially greater than the width of the base panel 12.

At the free end of the base portion 12 is an end panel 26 joined at its captive edge to a corresponding edge of the base along a fold line 27. The fold line 27 is in alignment with an end edge 28 of the side panel 18 and a similar end edge 29 of the side panel 22.

At the opposite end of the package there is another end panel 30 joined at its captive edge to a corresponding edge of the base portion 11 along a fold line 31. The fold line 31 is in alignment with an end edge 32 of the side panel 14 and a corresponding end edge 33 of the side panel 20.

One of the end panels, namely, the end panel 30 as shown, provides for attachment of a specimen strip 35, a specimen strip customarily being a transparent glass or plastic strip for reception of the physical specimen for which analysis is sought. As shown in the form of invention of FIG. 1, the end panel 30 is provided with a slot 36 long enough to accommodate the width of the specimen strip and wide enough to comfortably accommodate the thickness.

In the embodiment shown there is a bar 37 forming one side of the slot 36 and a second bar 38 forming the other side, the bar 38 being separated by a slit 39. At the relative mid-portion of the end panel 30 there is provided a window 41. The window has a length approximately equal to the length of the slot 36 and a width substantially greater. Beneath the window is a space 42 which is provided for identification of the specimen which is to be collected on the specimen strip 35.

By providing retention means on the end panel 30 for the specimen strip 35 in the form and manner described, the specimen strip can be attached to the end panel when the panel is in open position, and then the tab with the strip swung over the corresponding face of the bottom portion 11. Insertion and removal of the strip can also take place when the end panel is folded over. By having the specimen strip capable of being lifted with the end panel, there is ready access to the space 42 for specimen identification insignia 42', after which it is covered over by replacement of the strip and end panel.

It is additionally noteworthy to have cuts 43 and 44 extending partway along the length of the fold line 31. With the fold line cut in this fashion, the end panel and connected specimen strip can be more readily compacted in final position during the packaging. There is a comparable advantage in the provision of a score line 45 operable when the initial package is closed. The end panel 30 with a single window 41 is by way of example only. On occasion two windows each with a strip may be preferred. The side panels 14 and 20 also provide package material where windows and strip may be located, if desired, assisted if need be with cuts like the cuts 43 and 44 which assist the end panel 30.

For closing and holding the package in closed position, the side panel 14 is provided with a slightly arcuate slit 48, with an escape slit 49 extending to the free edge 16. There is a comparable slit and escape slit for the side panel 18. On the opposite side of the base portion 11, the side panel 20 is provided with a flap 50 on a corresponding free edge 51. The side panel 20 has notches 52 and 53 at opposite ends of the flap 50 notches determine an effective length for the flap as being slightly greater than the length of the slit 48 when the flap is interlocked with the slit. The side panel 22 is similarly equipped.

It has been found advantageous to have the aggregate width of the side panel 20 and the distance between the fold line 15 and the slit 48 slightly greater than the width of the base portion 11. Dimensioned as described, coupled with a slight folding at the score line 45, provides for a space beneath the side panels 14 and 20 when they are folded over each other to allow for accommodation not only of the specimen strip 35, but other paraphernalia which may be initially contain within the package such, for example, as a swab 46, tongue depressor 47 and fixative package 40.

There is additionally provided a line of perforations between the base portion 11 together with its side panels 14 and 20, and the base portion 12 together with its side panels 18 and 22. A central section 54 of the line of perforations separates the base portion 12 from an auxiliary end panel 55. Side sections 56 and 57 of the line of perforations defines side edges of the auxiliary end panel 55. A section 58 of the line of perforations separates the side panels 14 and 18 and a section 59 separates side panels 20 and 22.

When the full size of the package as shown in FIG. 3 is no longer needed, the package is separated along the lines of perforations just described so that the base portion 11 with its newly acquired auxiliary end panel 55 can be made into a smaller separate package as shown in FIG. 8 completed by the presence of the folded-over side panels 14 and 20. The base portion 12, with its side panels 18 and 22 and end panel 26 being no longer needed, may be disposed of, together with such paraphernalia as may initially have been needed. Under these circumstances, the smaller of the packages which contains the specimen strip 35 and its identification is readily closeable for transportation and storage until needed.

In a second form of the invention, an end panel 30' is shown provided with a window 61 formed by side edges 62 and 63 with an end edge 64. Tabs 65 and 66 are located on corresponding side edges 62 and 63 and provide for retention of the specimen strip 35. There is abundant space beneath the window for use in identification.

In another form of the device, an end panel 30'' is shown provided with diagonally disposed slits 68, 69 for retention of the specimen strip 35. A space 70 on the corresponding face of the end panel serves for use in identification of the specimen.

Figure 13:
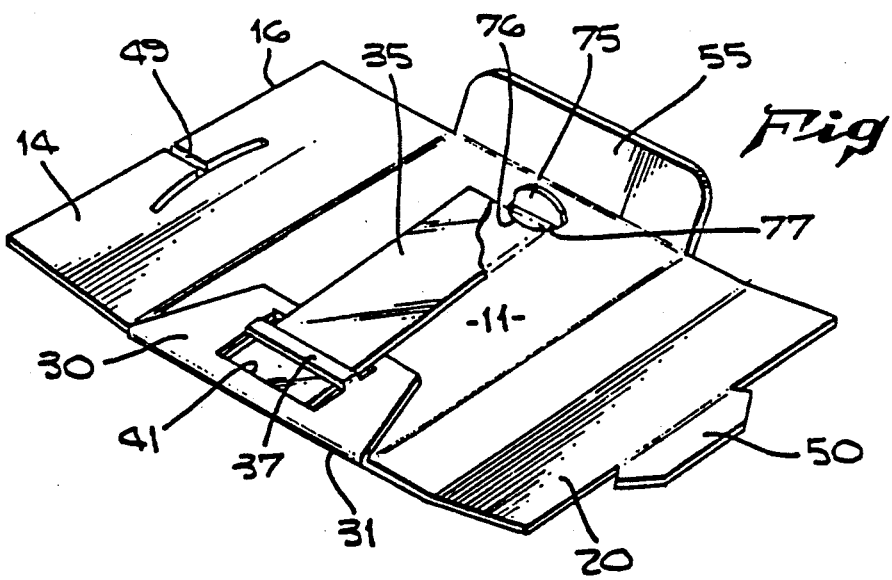
FIG. 13 is a perspective view similar to FIG. 12 wherein the slide is shown in place.
Figure 14:
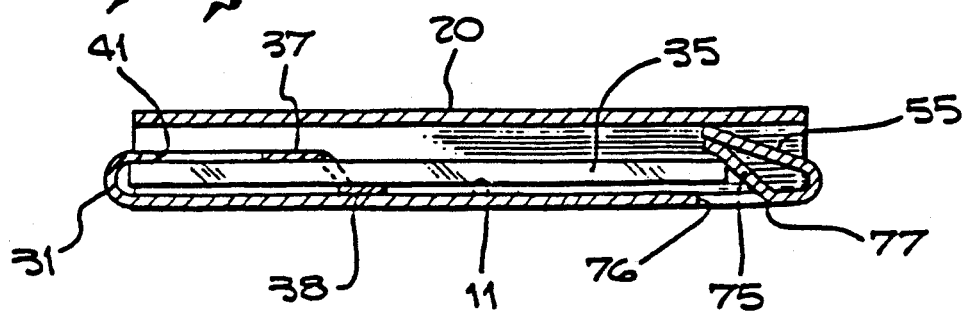
FIG. 14 is a cross-sectional view of the final package of the modified form of FIGS. 12 and 13.
Figure 15:
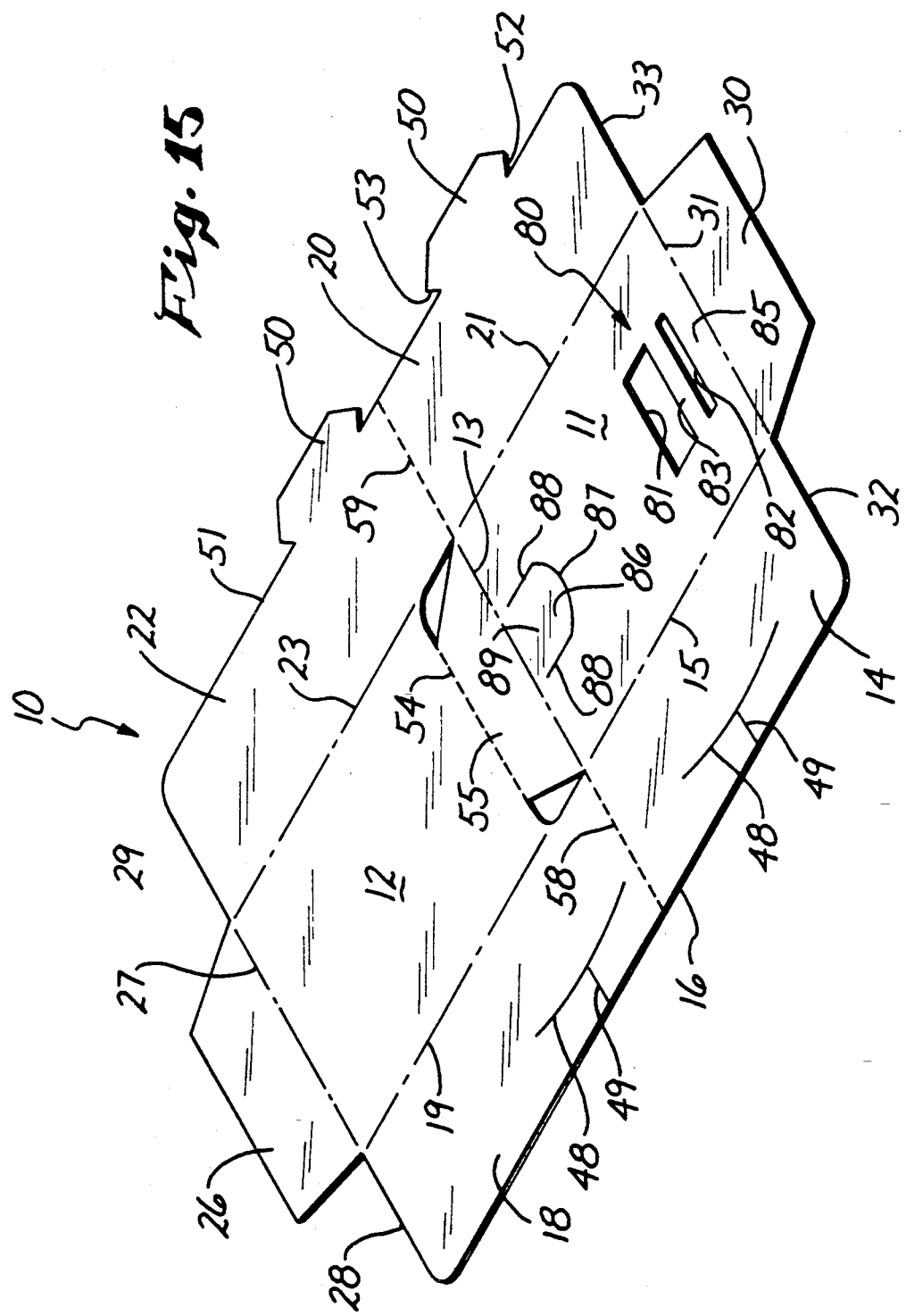
FIG. 15 is a perspective view of a fourth form of the sheet of material used to package the specimen strip.

In the form of the device of FIGS. 12, 13 and 14, use is made of a holding tab 75 for additional retention of the otherwise free end of the specimen strip 35. The holding tab shown by way of example is cut from the base portion 11 along an arcuate line 76. A folding line 77 of the holding tab is at a location adjacent to or slightly beyond the position the free end of the specimen strip will have when the package is closed for shipping. In this position the holding tab will be capable of pressing firmly against the specimen strip, with the assistance of the auxiliary end panel 55 and one or another of the side panels 14, 20. Retention of the free end edge of the specimen strip is effective in preventing endwise shifting when packaged.

FIGS. 15 through 18 show an alternate form of the invention where the retaining means for engaging the specimen strip are provided on the central base portion 11, instead of being provided on the end panel 30, as was the case in the embodiments illustrated in FIGS. 1 through 14. Common elements are shown by the same numerals in all forms of the invention shown in the drawings. A first retainer for the specimen strip is generally designated by the numeral 80 in FIG. 15 and includes two openings 81, 82 defined in the central base portion 11 of the package sheet. Both openings are of rectangular shape and are separated by a relatively narrow strip 83 which is integral with the base portion 11. The length of both openings 81, 82, as measured between the side panels 14, 20, is slightly greater than the width of the specimen strip 35, so as to hold the strip against significant lateral movement when placed in the retainer in a manner which will be explained below:

The width of openings 81, 82 measured between end panels 30, 55, differs for the two openings. Opening 81, 82 is sufficiently wide to readily accommodate the thickness of the specimen strip 35 when one end of the strip is inserted through this opening. The opening 81, however is considerably wider, approximately three times the width of opening 82. The strip 83 may be about one and half times the width of opening 82. The retainer 80 engages one end of the specimen strip 35 in a manner illustrated in FIGS. 16 and 18.

The medical specimen strips typically used for collection of biological samples taken from patients typically have a frosted surface at one end of the slide. The frosted surface allows writing on the surface by medical personnel collecting the specimen in order to identify the nature and/or source of the biological specimen on the strip 35. Typically, it is the frosted end strip 35 which is engaged to the retainer 80. The strip 35 is engaged to the retainer 80 by first inserting the end 84 into opening 81, pushing the end 84 under the strip 83 and then threading the end 84 upwardly into and through opening 82. Engagement of the strip 35 is then completed by pushing the strip 35 a short distance towards the end panel 30 until the end 84 rests on and is supported by the end support area 85 of the base portion 11 which lies between the opening 82 and the fold line 31 of end panel 30. The end 84 of the slide 35 is shown in this engaged condition in FIGS. 16 and 18. The strip 83 snugly spans the width of the strip 35 and securely retains it flat against the central base portion 11. The specimen strip 35 is held in bridging relationship across both openings 81, 82 when engaged to the first retainer 80. In this condition, the specimen strip extends across both openings between the central area of the base portion 11 and the end support area 84, underneath the retaining strip 83. Inasmuch as the length of the strip 83 is only slightly greater than the width of the specimen strip 35, the retaining strip 83 has a snug frictional hold on the strip 35 and will normally suffice to hold the specimen strip 35 against significant movement in a longitudinal direction through the retainer 80.

Figure 17:
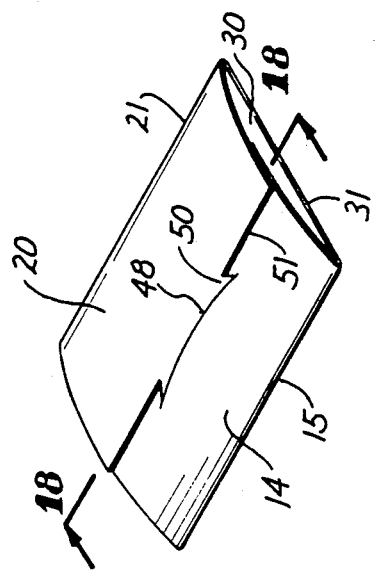
FIG. 17 is a perspective view of the solid lined portion of the sheet of FIG. 16 folded to its packaged position.
Figure 18:
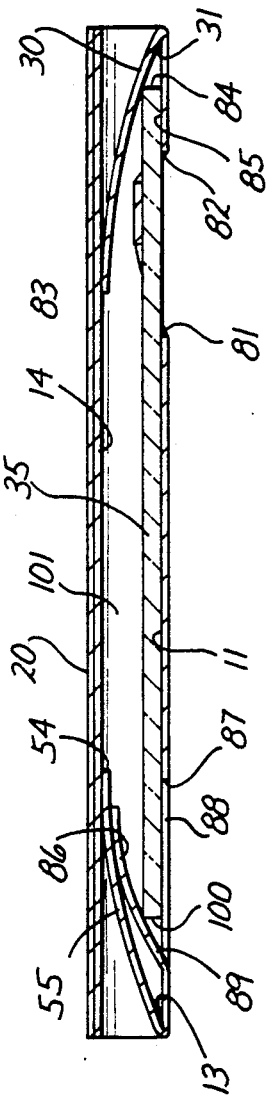
FIG. 18 is a cross section taken along line 18—18 in FIG. 17.

The specimen strip 35 is further secured in place by the end panel 30 which holds down the end 84 of the strip in the folded, packaged condition of the sheet shown in FIGS. 17 and 18. FIG. 18 shows how the strip end 84 lies close to the fold line 31 and is held between the end panel 30, which folds over the end 84 of the specimen strip, and the support area 85 under the panel 30. Consequently, the specimen strip 35 has limited if any room for longitudinal displacement towards the end panel 30, in the packaged condition of FIG. 18.

Figure 16:
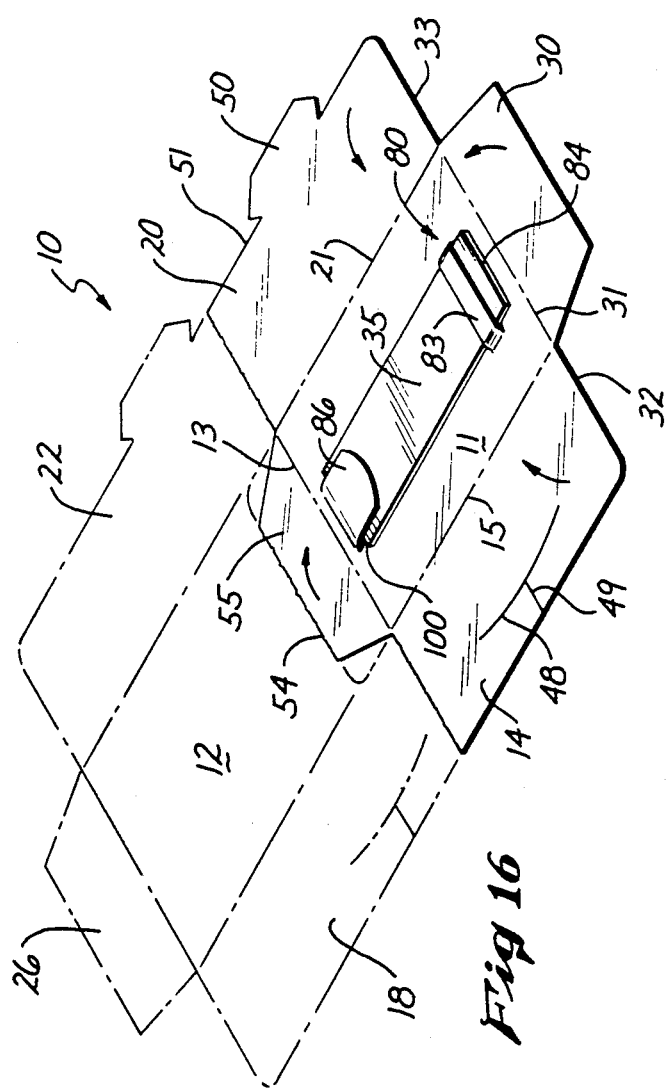
FIG. 16 is a view as in FIG. 15, showing in solid lining that portion of the sheet used for the final package, the portion of the sheet shown in phantom lining being separated for packaging the specimen strip.

A second retainer in the form of tab 86 is defined integrally with the base portion 11 by an arcuate slit line 87 connecting the ends of two parallel slits 88. The tab 86 is connected to the central base portion at an end 89. The free end of the tap defined by the slit line 87 can be lifted from the central base portion, and an opposite end 100 of the specimen strip 35 captured under the tab 86, in a manner shown in FIGS. 16 and 18. The tab 86 tends to hold down the opposite end 100 of the specimen strip 35 against the base portion 11, and also holds the specimen strip 35 against sliding movement through the first retainer 80, under the strip 83 towards the end panel 55, as best seen in FIGS. 16 and 18. In the packaged condition shown in FIGS. 17 and 18, the end panel 55, when folded along fold line 13 bears down on the free end of the tab and assists in holding down the strip end 100 against the central base portion 11.

The side panels 14 and 20 have a combined width, in the packaged condition of the package sheet 10, which is greater than the width of the central base portion 11 between these panels. Consequently, when the flap 50 is engaged to the slit 48, as in FIG. 17, the side panels 14, 20 are forced to an arcuate configuration which is concave on the interior side of the package, so that the side flaps raised away from the specimen strip 35 supported on the base portion 11. This creates an interior space 101 above the specimen strip 35 which tends to protect and preserve the biological specimen carried on the specimen strip. The end flaps 30, 55 contribute in supporting the side flaps 14, 20 in this arcuate configuration by pushing up on the underside of the side flaps in the packaged condition of the sheet 10.

It must be understood that the specimen strip retainer 80 can be positioned at different locations on the sheet 10 in addition to the two positions illustrated in the drawings, i.e. on the end flap 30 and on the central base portion 11 adjacent to the end flap 30. Also, the first specimen strip retainer 80 may be used with or without the second retainer or tab 86.

While particular embodiments of the present invention have been shown and described, it will be obvious to those skilled in the art that changes and modifications may be made without departing from the invention in its broader aspects and, therefore, the aim of its attendant claims is to cover all such changes and modifications as fall within the true spirit and scope of this invention.

Having described the invention, what is claimed as new in support of Letters Patent is as follows:

1. A specimen package assembly for containment of a medical specimen slide, said package assembly comprising:

a sheet of package material having a central base portion, a plurality of side panels and end panels joined to said central base portion, said side panels having latching means for holding all said panels in packaged condition;

retaining means including two rectangular openings in said central base portion separated by a retaining band for holding a said specimen slide against said base portion, said openings having a length between said side panels dimensioned for holding the width of a said slide against substantial lateral movement under said band;

said openings having different widths in a direction transverse to said retaining band, one of said openings having a width sufficient for accepting the thickness of a said slide, the other of said openings being at least twice as wide, said retaining band being narrower than said other of said openings.

2. The specimen package assembly of claim 1 wherein said openings are spaced from one of said end panels by a slide end supporting area of said base portion, such that a first end of a slide is engaged and supported on said base portion by inserting said first end through both said openings and under said band.

3. The specimen package assembly of claim 2 further comprising second retaining means defined in said central base portion adapted to engage a second end opposite said first end of a specimen slide for holding said second end to said central base portion.

4. The specimen package assembly of claim 3 wherein a said specimen is substantially contained against longitudinal displacement between said second retaining means and one of said end panels in said packaged condition of said sheet.

5. The specimen package assembly of claim 3 wherein said second retaining means includes a tab having a free end defined by cutting of said sheet.

6. The specimen package assembly of claim 5 wherein one of said end panels bears down on said free end of the tab and assists in holding said tab in engagement with said second end in said packaged condition.

7. The specimen package assembly of claim 1 wherein said base portion has a width between said side panels and, said side panels each being joined to said base portion by a single fold line between said base portion and said latching means, and said side panels have a combined width in said packaged condition greater than the width of said base portion, such that the side panels are forced into an arcuate condition between said fold lines away from a specimen slide supported by said retaining means to avoid contact with a biological specimen on said slide.

8. The specimen package assembly of claim 7 wherein said end panels are each joined to said base portion by a single fold line between said base portion and said latching means, said retaining means being positioned for placing opposite ends of a specimen slide closely adjacent to said single fold line of each end panel for supporting said end panels thereby to assist in maintaining said side panels in aid arcuate condition.

9. A specimen package assembly for containment of a specimen slide, said package assembly comprising:
a sheet of package material having a central base portion, a plurality of side panels and end panels joined to said central base portion, said side panels having latching means for holding all said panels in packaged condition;
retaining means including two rectangular openings in said central base portion separated by a retaining band for holding a specimen slide against said base portion, said openings having different widths as measured in a direction transverse to said retaining band, one of said openings having a width sufficient for accepting the thickness of said slide, the other of said openings being at least twice as wide;
the narrower of said openings being proximal to one of the panels, such that a slide may be inserted into the wider of said openings from the central base portion towards one of said end panels;
and wherein the narrower of said openings is spaced from said one of said end panels by a slide end supporting area of said base portion, such that an end of a slide is engaged and supported on said base portion by inserting the slide end through both said openings and under said retaining band.

10. A specimen package assembly for containment of a specimen slide, said package assembly comprising:
a sheet of package material having a central base portion a plurality of side panels and end panels joined to said central base portion, said side panels having latching means for holding all said end panels in packaged condition;
retaining means including two openings in said central base portion separated by a retaining band for holding a said specimen slide against said base portion, said openings having a length dimensioned between said side panels for holding the width of a said slide against substantial lateral movement under said band; and
a tab having a free end defined in said central base portion and adapted to engage an opposite end of said specimen slide for holding said opposite end to said central base portion; and
wherein one of said end panels bears down on said free end of the tab and assists in holding said tab in engagement with said opposite end in said packaged condition.

11. The specimen package of claim 1 wherein said base portion has a width between said side panels and said side panels having a combined width in said packaged condition grater than the width of said base portion, such that the side panels are forced into an arcuate condition away from a specimen slide supported by said retaining means to avoid contact with a biological specimen on said slide.

* * * * *